(12) United States Patent
Goodenough et al.

(10) Patent No.: US 9,093,692 B2
(45) Date of Patent: Jul. 28, 2015

(54) OXIDE-ION CONDUCTORS AND RELATED COMPOSITES AND DEVICES

(71) Applicants: John B. Goodenough, Austin, TX (US); Preetam Singh, Austin, TX (US)

(72) Inventors: John B. Goodenough, Austin, TX (US); Preetam Singh, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 149 days.

(21) Appl. No.: 13/967,152

(22) Filed: Aug. 14, 2013

(65) Prior Publication Data

US 2015/0050578 A1    Feb. 19, 2015

(51) Int. Cl.

| | |
|---|---|
| *H01M 8/10* | (2006.01) |
| *H01M 8/12* | (2006.01) |
| *C01F 17/00* | (2006.01) |
| *H01B 1/08* | (2006.01) |
| *G01N 27/406* | (2006.01) |
| *G01N 27/407* | (2006.01) |
| *C04B 35/01* | (2006.01) |
| *F02D 41/14* | (2006.01) |
| *C01B 13/14* | (2006.01) |
| *C04B 35/047* | (2006.01) |
| *H01B 1/12* | (2006.01) |

(52) U.S. Cl.
CPC .......... *H01M 8/1246* (2013.01); *C01F 17/0018* (2013.01); *C01F 17/0043* (2013.01); *C04B 35/01* (2013.01); *F02D 41/1438* (2013.01); *G01N 27/406* (2013.01); *G01N 27/4073* (2013.01); *H01B 1/08* (2013.01); *H01M 8/1004* (2013.01); *H01M 8/12* (2013.01); *C01B 13/14* (2013.01); *C04B 35/047* (2013.01); *H01B 1/122* (2013.01); *H01M 2008/1293* (2013.01); *H01M 2300/0074* (2013.01)

(58) Field of Classification Search
USPC ............ 429/495, 188, 304; 252/518.1, 521.1; 423/263; 204/410, 421, 424
See application file for complete search history.

(56) References Cited

FOREIGN PATENT DOCUMENTS

| | | |
|---|---|---|
| EP | 1 168 478 A2 | 1/2002 |
| EP | 1 300 365 A2 | 9/2002 |
| EP | 1 351 326 A2 | 10/2003 |
| EP | 1 447 818 A2 | 8/2004 |
| JP | 2009046354 A * | 3/2009 |

OTHER PUBLICATIONS

Ishihara et al. "Improved Oxide Ion COnductivity in La0.8Sr0.2Ga0.8Mg0.2O3 by Doping Co", CHem. Mater., 1999, 11 (8), pp. 2081-2088 (web publication date Jul. 28, 1999).*

PCT International Search Report and Written Opinion in International Application No. PCT/US2014/050765, mailing date Nov. 4, 2014, 11 pages.

(Continued)

*Primary Examiner* — Gregg Cantelmo
(74) *Attorney, Agent, or Firm* — Baker Botts L.L.P.

(57) ABSTRACT

The present disclosure relates to an oxide-ion conductor having the general formula $La_2Ge_{1-x}Cr_xMgO_{6-0.5x}$, where $0<x<1$ and M=Cr, Sc, Ga and In or a mixture thereof. The present disclosure further relates to composite materials containing such oxide-ion conductors and to devices containing such oxide-ion conductors or composites.

18 Claims, 5 Drawing Sheets
(3 of 5 Drawing Sheet(s) Filed in Color)

(56) References Cited

OTHER PUBLICATIONS

Ishihara T. et al., "Doped LaGa03 perovskite type oxide as a new oxide ionic conductor", Journal of the American Chemical Society, ACS Pulbications, vol. 116, No. 9, Jan. 1, 1994, pp. 3801-3803.

Preetam Signh et al., "Monoclinic Sr1-x NaxSio03-0.5x: New Superior Oxide Ion Electrolytes", Journal of the American Chemical Society (JACS), received May 6, 2013, 6 pages.

* cited by examiner

OXIDE-ION CONDUCTORS AND RELATED COMPOSITES AND DEVICES

TECHNICAL FIELD

The present disclosure relates to oxide-ion conductors having the general chemical formula $La_2Ge_{1-x}M_xMgO_{6-0.5x}$, in which $0<x<1$ and M=Cr, Sc, Ga and In or a mixture thereof.

BACKGROUND

The ability to conduct oxide-ions ($O^{2-}$) allows the use of materials in a variety of applications. For instance, such materials may be used in solid oxide fuel cells, as oxygen sensors, in oxygen separation membranes, in hydrogen production from water, and in any other use where the movement or detection of oxide-ions is desirable.

Many oxide-ion conductive materials have been developed, but they often are too reactive with other components in the systems where they may be used, are not able to tolerate high temperatures, or simply fail to have a high enough oxide-ion conductivity.

For example, one current oxide-ion conductor, which has the general chemical formula $La_{0.8}Sr_{0.2}Ga_{0.83}Mg_{0.17}O_{2.815}$, has an oxide-ion conductivity ($\sigma_O$) of greater than $10^{-2}$ Siemens per centimeter (S/cm) only at temperatures above 600° C. Another oxide-ion conductor, with the general formula $Sr_{0.8}K_{0.2}Si_{0.5}Ge_{0.5}O_{2.9}$, which is representative of oxide-ion conductors with the general formula $Sr_{1-x}A_xSi_{1-y}Ge_yO_{3-0.5x}$ have an oxide-ion conductivity ($\sigma_O$) of greater than $10^{-2}$ S/cm only above temperatures around 625° C. A third type of oxide-ion conductors, with the general formula $Sr_{0.6}Na_{0.4}SiO_{2.8}$ or the general formula $Sr_{0.55}Na_{0.45}SiO_{2.775}$, have an oxide-ion conductivity ($\sigma_O$) of greater than $10^{-2}$ S/cm above temperatures around 525° C.

Additional super oxide-ion conductors, particularly those with an oxide-ion conductivity ($\sigma_O$) of greater than $10^{-2}$ S/cm at lower temperatures are needed.

SUMMARY

The present disclosure relates to an oxide-ion conductor having the general formula $La_2Ge_{1-x}M_xMgO_{6-0.5x}$, M=Cr, Sc, Ga and In or a mixture thereof in which $0<x<1$. The present disclosure further relates to composite materials containing such oxide-ion conductors and to devices containing such oxide-ion conductors or composites containing these oxides.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Embodiments of the disclosure may be better understood through reference to the following figures, in which.

DETAILED DESCRIPTION

Figure 1:
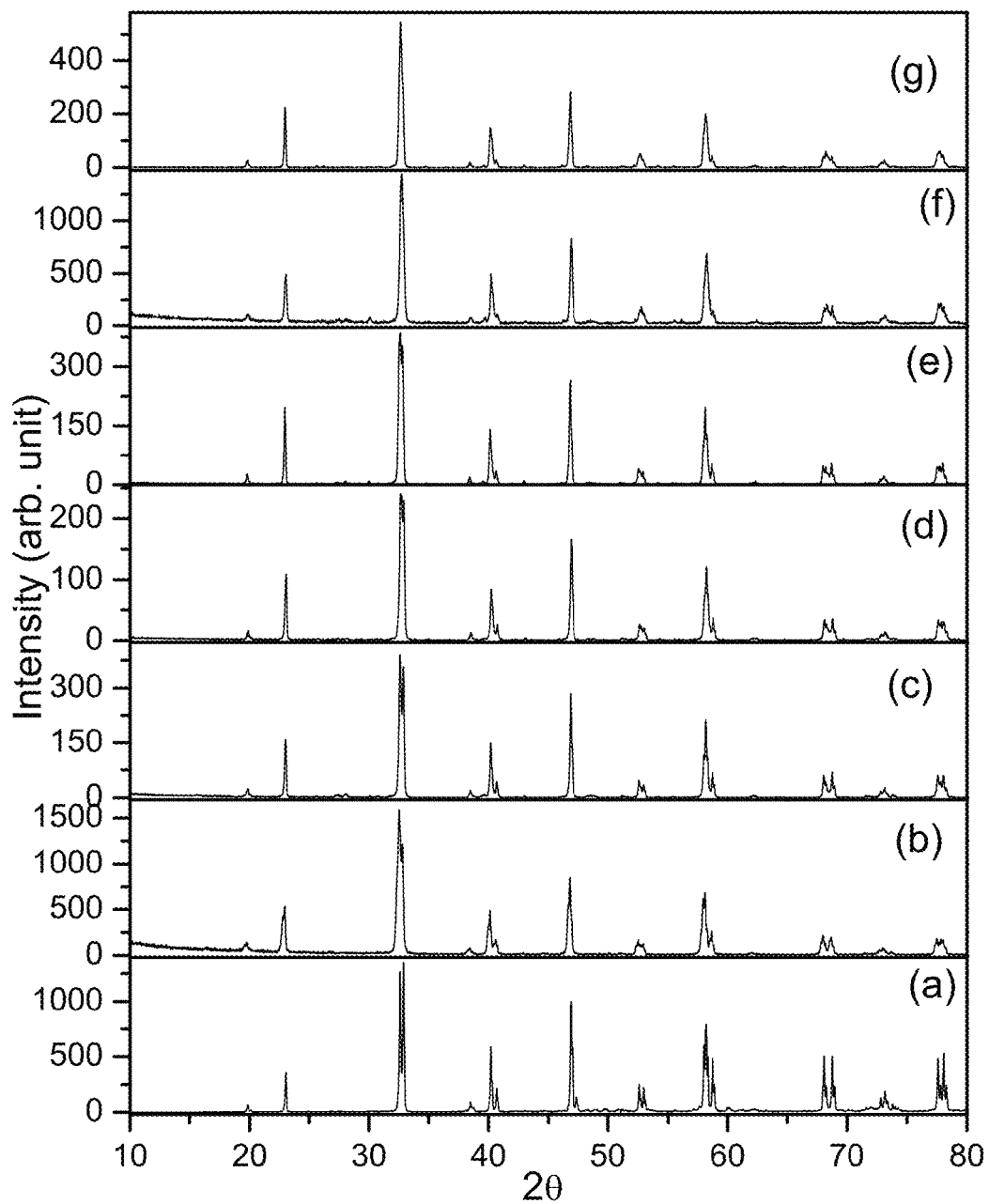
FIG. 1 presents X-ray diffraction (XRD) patterns of oxide-ion conductors having the general formula $La_2Ge_{1-x}Cr_xMgO_{6-0.5x}$, in which x is between 0 and 0.5; in (a) x=0, in (b) x=0.2, in (c) x=0.35, in (d) x=0.4, in (e) x=0.45 and in (f) x=0.5.

The present disclosure relates to oxide-ion conductors having the general chemical formula $La_2Ge_{1-x}M_xMgO_{6-0.5x}$, (M=Cr, Sc, Ga, In or a mixture thereof) in which $0<x<1$, or in some embodiments, $0<x\leq0.5$.

The oxide-ion conductors may be single-phase solid materials with a perovskite or perovskite-related crystal structure, with elemental substitutions and distortions or other changes in lattice parameters dictated by the actual composition of any particular oxide-ion conductor, for example in accordance with principles that may be derived from Table 1. In general, the crystal structure of the oxide-ion conductors may be similar to that of $La_2GeMgO_6$, but without ordering of $Mg^{2+}$ and $Ge^{4+}$ ions. Doping with $M=M^{3+}$ introduces oxide-ion vacancies that are mobile. Oxide-ion conductors of the present disclosure may be in the form of a single crystal or a polycrystalline ceramic or a composite.

Oxide-ion conductors of the present disclosure may have an oxide-ion conductivity ($\sigma_O$) up to $10^{-2}$ S/cm at temperatures above 300° C. and up to $10^{-4}$ S/cm at room temperature.

Oxide-ion conductors of the present disclosure may be used in any of the applications described herein at temperatures greater than or equal to room temperature.

In general, increased amounts of chromium (Cr) in oxide-ion conductors with the general chemical formula $La_2Ge_{1-x}Cr_xMgO_{6-0.5x}$ may result in higher oxide-ion conductivity ($\sigma_O$) at a given temperature as compared to oxide-ion conductors for the lower values of x or those lacking chromium.

The present disclosure also relates to oxide-ion conducting composites containing an oxide-ion conductor as described herein in combination with one or more other materials. The other materials may include different electrode materials, sintering agents, binders, impurities, or stabilizing electronic insulators. In specific embodiments, the oxide-ion conducting composites may include at least sufficient oxide-ion conductor, as described herein, for percolation of oxide-ions.

Fuel Cells

According to one embodiment, the present disclosure includes a solid oxide fuel cell containing an oxide-ion conductor as described herein. As the electrolytes, such a fuel cell may operate by extracting electrical energy from the chemical reaction of a fuel, such as hydrogen or a hydrocarbon gas, with oxygen in the air. This electrical energy is compatible with existing electrical systems, such as systems that run off batteries or household electricity. For example, electrical energy generated using a fuel cell may be used to run household or small appliances or consumer electronics or for larger applications, such as in generators or automobiles.

In a specific embodiment, the fuel cell may operate on hydrogen gas, rendering it environmentally friendly because the primary by-product of its operation is simply water. In another embodiment, the fuel cell may use hydrocarbons instead of hydrogen gas.

In another embodiment, the oxide-ion conductor may be used in a regenerative fuel cell or reverse fuel cell (RFC), which is a fuel cell run in reverse mode, thereby consuming electricity and chemical B to produce chemical A (e.g. a regenerative hydrogen fuel cell may use electricity and water to produce hydrogen and oxygen). For example, the regenerative fuel cell may be a solid oxide electrolyzer cell used to produce hydrogen gas from water.

Fuel cells or regenerative or reverse fuel cells using oxide-ion conductors as described herein may be able to operate at temperatures at or greater than room temperature.

Figure 5A:
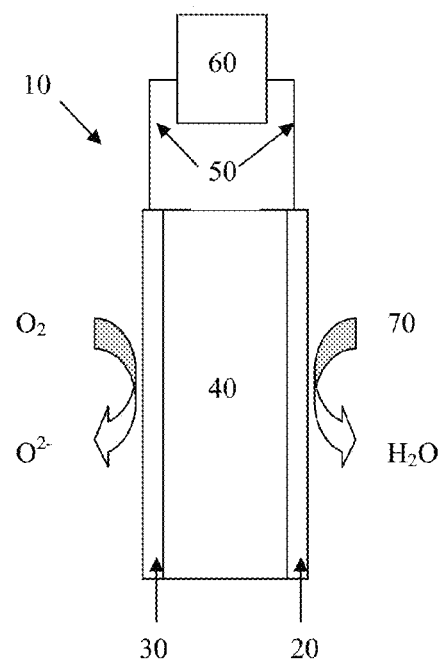
FIG. 5A illustrates the basic components and reactions of a solid oxide fuel cell operating on $H_2$ gas.
Figure 5B:
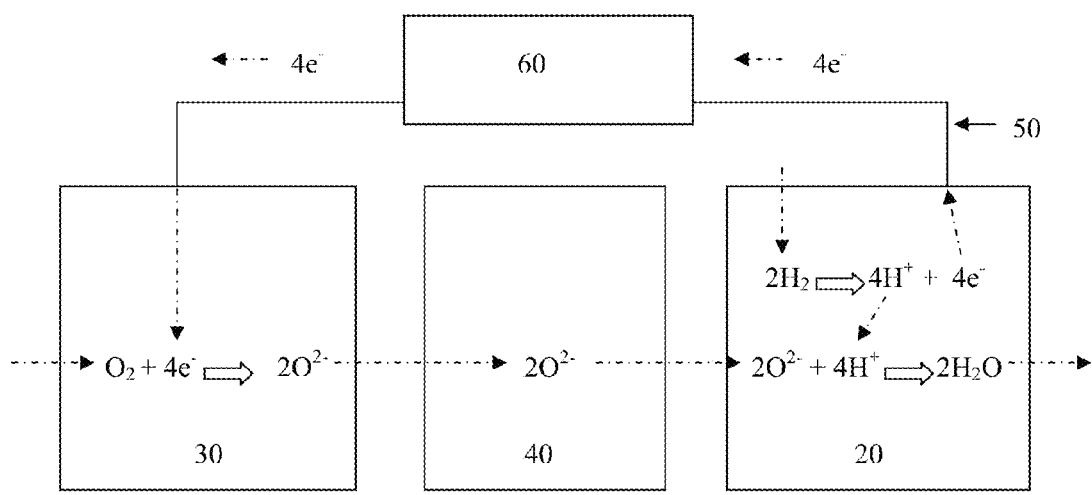
FIG. 5B illustrates the chemical reactions taking place in and movement of hydrogen fuel, oxygen gas, electrons and oxide-ions in a solid oxide fuel cell.

FIG. 5A illustrates a solid oxide fuel cell 10. Solid oxide fuel cell 10 contains an anode 20, a cathode 30 and an electrolyte 40. Solid oxide fuel cell 10 also contains leads 50, which may be connected to a device 60 powered by the fuel cell.

When solid oxide fuel cell 10 is in operation, three chemical reactions take place, typically at the same time or nearly the same time. These chemical reactions and the movement of participants in these reactions are further illustrated in FIG. 1B. With hydrogen gas as fuel, hydrogen ($H_2$) from a fuel source reacts with the anode to form hydrogen ions ($H^+$) and free electrons ($e^-$). These free electrons move through the leads 50 to the cathode, powering device 60 in the process. Oxygen ($O_2$_) in the air reacts with cathode 30 to accept four free electrons ($e^-$) from leads 50 to form two oxide-ions ($O^{2-}$). The oxygen ions enter the electrolyte 40. Electrolyte 40 contains an oxide-ion conductor of the present disclosure. Thus, when two oxide-ions enter electrolyte 40 at the cathode, two oxide-ions are able to leave electrolyte 40 at the anode. These oxide-ions react at the anode to form water with the hydrogen ion from $H_2$ in the first reaction, the third chemical reaction taking place in the fuel cell to form water.

Electrolyte 40 in fuel cell 10 may contain, in addition to an oxide-ion conductor according to the present disclosure, other component materials to stabilize the solid crystal in the fuel cell, binders, and any other components suitable for addition to solid oxide-ion conducting materials. Electrolyte 40 may include the oxide-ion conductor in the form of a ceramic or composite membrane such as sheet, or other solid member able to block the passage of electrons within the electrolyte between the anode and cathode. The membrane, sheet, or other solid member may contain a non-electrolyte material. Such material may provide structural support or integrity to the membrane or other solid material. Such material may include a binder, such as a polymer. The membrane or solid member may be an electronic insulator. The electrolyte may also form a composite with an electrode.

Anode 20 may contain any material suitable to cause the removal of electrons from hydrogen or a hydrocarbon fuel to result in hydrogen ions and free electrons. For example, anode 20 may include any material suitable for use in other solid oxide fuel cells. In one embodiment, anode 20 may include a material able to catalyze the formation of chemisorbed hydrogen and or chemisorbed hydrocarbon ions from hydrogen gas or a hydrocarbon fuel. The catalytic material or another additive material in the anode may also be electrically conductive.

In one embodiment, the anode 20 may include a cermet (ceramic metal) material, such as a nickel-based cermet material. The ceramic portion of the anode may include one or more materials also found in the electrolyte.

Fuel 70 may be hydrogen or a hydrocarbon gas. If the hydrocarbon fuel is methane, propane, or butane, in some embodiments, it may simply be supplied to the anode and able to react with the anode without prior processing. The hydrocarbon fuel may be processed in or near the fuel cell, prior to or at the same time as contact with the anode, to facilitate its interaction with the anode to produce hydrogen ions. For example, the hydrocarbon fuel may be reformed or processed to remove sulfur.

Cathode 30 may contain any material suitable to cause the addition of electrons to oxygen gas in the air to form oxide-ions. For example, cathode 30 may include a catalytic material able to catalyze the formation of oxide-ions. The catalytic material or other additive material may also be electronically and oxide-ion conductive.

In one embodiment, the cathode 30 may contain a lanthanum manganite, particularly a lanthanum or rare-earth manganite doped with an alkaline element (e.g. Sr) to increase its electrical conductivity, such as $La_{1-x}Sr_xMnO_3$. Cathode 30 may also contain other air-reactive materials, such as mixed electronic/oxide-ion conductors.

Anodes and cathodes may both be formed as porous structures to facilitate the movement of fuel, air, water or other wastes like carbon dioxide or water through the electrode. Anodes and cathodes may have microstructures designed to facilitate catalytic activity or overall fuel-cell performance. Anodes and cathodes may include binders and conductive additives. In any fuel cell, anode 20 and cathode 30 may be either directly or indirectly in electrical contact with leads 50.

Anode 20, cathode 30 and electrolyte 40 must function within certain compatible parameters to form a functional fuel cell. Furthermore, the choice of different anodes/cathode/electrolyte combinations may affect an electrical parameter of the fuel cell, such as power or power density. The chosen combination may also affect other performance parameters, such as compatible fuels, suitable operating conditions, and usable life. In one embodiment, a longer-life, lower-cost fuel cell may be created by avoiding the use of platinum or similar noble metals as a catalyst material. Fuel cells using an electrolyte of the present invention may also allow the use of catalyst materials in the anode or the cathode that are not usable in many present solid oxide fuel cells due to incompatibilities with the higher temperatures at which such cells operate.

A fuel cell 10 of the present disclosure may be formed in a wider variety of shapes than fuel cells that contain liquid electrolytes. In one embodiment they may be in a generally tubular shape, allowing the flow of fuel through the inside and air through the outside or vice versa. In another embodiment, fuel cells may be stacked electrolyte planes and may contain an interconnect layer of conductive material to allow them to be electrically connected.

In general, due to the relatively low voltage generated by most fuel cells, they may be electrically connected in series to allow increased voltage from a system containing multiple fuel cells.

The reactions that result in water in a fuel cell are exothermic. A fuel cell 10 of the present disclosure may be configured to allow use of this heat for other processes connected to fuel cell operation. Similarly, a fuel cell 10 of the present disclosure may be configured to allow use of by-product water for other processes connected to fuel cell operation.

Oxygen Sensors

In one embodiment, oxide-ion conductors described herein may be used in an oxygen sensor, particularly in an oxygen sensor designed for sensing oxygen content in a high temperature environment, such as in molten metals and alloys. This type of oxygen sensor may be particularly useful in connection with industrial steel production. Monitoring of oxide-ions in molten metal, particularly real-time monitoring, may allow the adjustment of process parameters to avoid or decrease the formation of unwanted by-products and internal structures, such as micro-structures within the metal. Sensors currently in use often employ solid electrolytes to sense oxide-ions. Oxide-ion conductors of the present disclosure may be used in such oxygen sensor at or above room temperature. Oxygen sensor solid electrolytes may also contain other components, such as additional electrolytes, materials to stabilize the solid crystal in the sensor, binders, and any other components suitable for addition to solid oxide-ion conducting materials.

Oxygen sensors using oxide-ion conductors as described herein may be able to operate at room temperature or at higher temperatures. The ability of such sensors to operate at low temperatures may allow expanded monitoring of molten metals during heating or cooling stages as compared to what is possible with conventional sensors.

Batteries

In another embodiment, the oxide-ion conductor may be used in a battery to store electrochemical energy. The battery may contain a fuel cell and metal/oxide bed. Such a battery may produce electricity for the fuel cell and oxidize the bed on discharge while in a fuel cell mode. The fuel cell may also operate in a regenerative mode to generate hydrogen while charging that reduces the oxide bed back to a metal.

In another embodiment, the oxide-ion conductor may be used in a reversible oxide-ion battery. Such a battery may contain a reductant anode, such as a metal and carbon composite anode. The metal may include lithium (Li) or sodium (Na). The battery may also include a catalyzing current collector cathode and an electrolyte membrane including an oxide-ion conductor as described herein. The electrolyte membrane may separate the cathode and the anode.

Other Applications

In still another embodiment, oxide-ion conductors of the disclosure may be used as a catalyst for the partial oxidation of olefins, which is a component of many industrial processes.

In a further embodiment, oxide-ion conductors of the disclosure may be used as a membrane in hydrogen production from steam electrolysis.

Additional embodiments may use oxide-ion conductors of the disclosure in microelectronics.

In another embodiment, oxide-ion conductors of the disclosure may be used in an oxygen-separation membrane. For example, they may be used in oxygen-separation membranes designed to reduce carbon dioxide emissions, such as from gas- or coal-fired power plants.

In all of the above applications, use of oxide-ion conductors as described herein may allow operation at room temperature or greater, which may represent an expansion of the applications and operation temperatures as compared to similar applications using current materials and devices.

EXAMPLES

The present invention may be better understood through reference to the following examples of the typical oxide-ion conductors of the invention. These examples are included to describe exemplary embodiments and comparative examples only and should not be interpreted to encompass the entire breadth of the invention.

XRD Analysis

Oxide-ion conductors having the general formula $La_2Ge_{1-x}Cr_xMgO_{6-0.5x}$, in which $0<x\leq0.5$ were formed and subjected to X-ray diffraction (XRD) with a Philips X'pert diffractometer (Cu Kα radiation, $\lambda=1.5418$ Å) in Bragg-Brentano reflection geometry. Results are presented in FIG. 1 and Table 1. The results confirm that the oxide-ion conductors all have a single-phase perovskite crystal structures similar to that of $La_2GeMgO_6$.

TABLE 1

Structural Parameter of $La_2Ge_{1-x}Cr_xMgO_{6-0.5x}$, in which $0 < x \leq 0.5$

| Compound | Lattice Parameter Å (a) | Lattice Parameter Å (c) | Cell Volume (Å³) | $\chi^2$ | $R_f$ | $R_{Bragg}$ | $R_{wp}$ |
|---|---|---|---|---|---|---|---|
| $La_2Ge_1MgO_6$* | 5.5125(1) | 13.3295(2) | 351.32 | | | | |
| $La_2Ge_{0.8}Cr_{0.2}MgO_{5.9}$ | 5.5184(3) | 13.3495(1) | 351.93 | 2.301 | 5.45 | 8.87 | 26.4 |
| $La_2Ge_{0.7}Cr_{0.3}MgO_{5.85}$ | 5.5172(2) | 13.3491(5) | 351.8 | 5.16 | 5.28 | 7.98 | 22.7 |
| $La_2Ge_{0.65}Cr_{0.35}MgO_{5.825}$ | 5.5159(4) | 13.3565(3) | 351.93 | 0.38 | 6.64 | 7.9 | 24.6 |
| $La_2Ge_{0.6}Cr_{0.4}MgO_{5.8}$ | 5.5149(2) | 13.3508(3) | 351.92 | 0.69 | 6.83 | 9.04 | 27.3 |
| $La_2Ge_{0.55}Cr_{0.45}MgO_{5.775}$ | 5.5155(2) | 13.3834(3) | 352.57 | 2.28 | 7.72 | 9.67 | 29.0 |
| $La_2Ge_{0.5}Cr_{0.5}MgO_{5.75}$ | 5.5149(3) | 13.3859(2) | 352.59 | 0.81 | 7.52 | 9.49 | 28.0 |

*Data reflects reference data published in *Chem. Commun.* 25: 1776-1777 (2002), incorporated in material part by reference herein.

Figure 2:
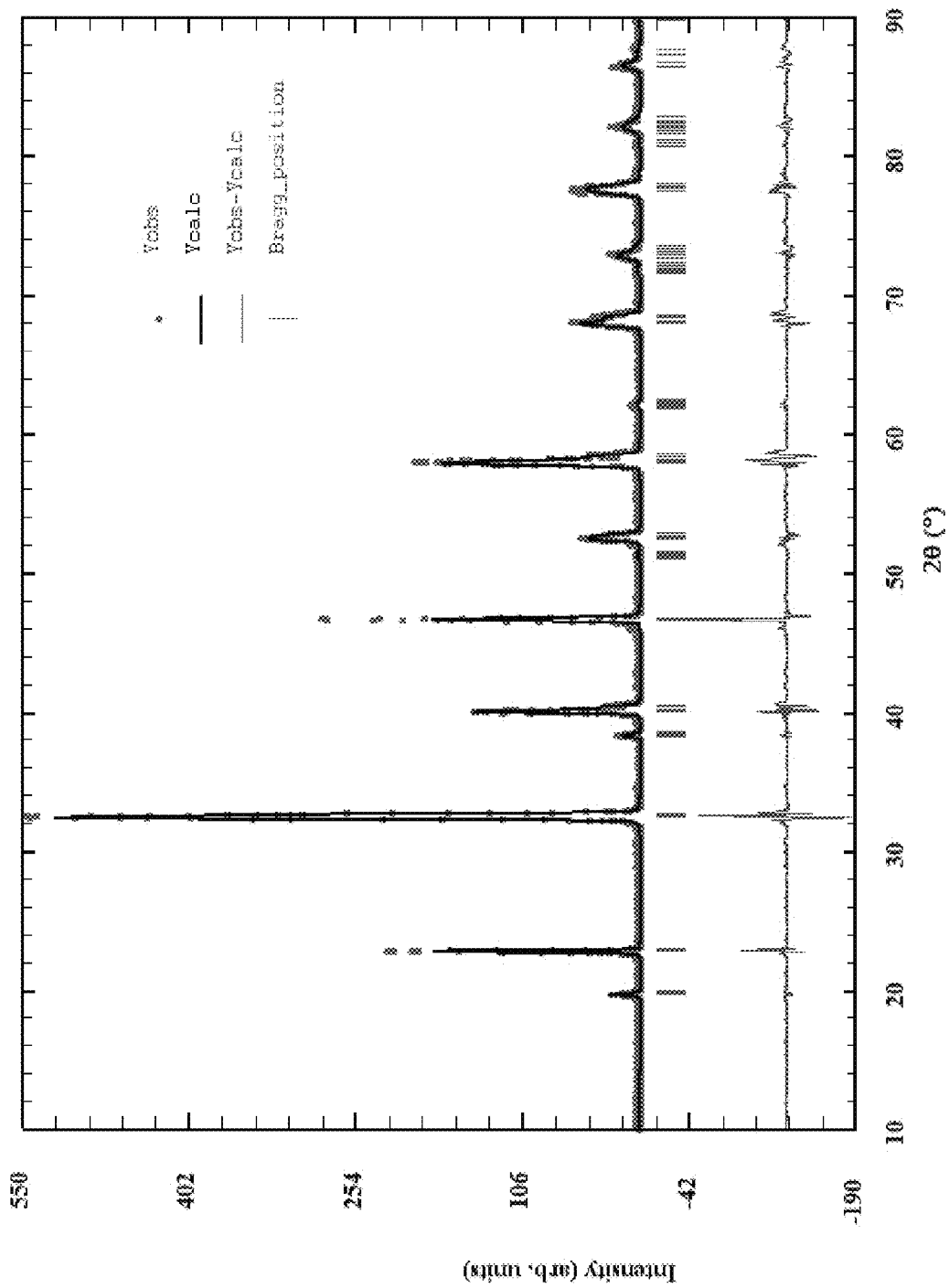
FIG. 2 presents a Rietveld refined XRD pattern of an oxide-ion conductor having the general formula $La_2Ge_{0.5}Cr_{0.5}MgO_{5.75}$.

A Rietveld structure refinement was carried out with the Fullprof program for an oxide-ion conductor having the general formula $La_2Ge_{0.5}Cr_{0.5}MgO_{5.75}$. Results are presented in FIG. 2. The fitted profile matches the observed XRD pattern well.

Oxide-Ion Conductivity ($\sigma_O$)

Two-probe AC impedance measurements of oxide-ion conductivity ($\sigma_O$) were made with a Solartron Impedance Analyzer (model 1287) (Hampshire, UK) operating in the frequency range of 1 Hz to 10 MHz with an AC amplitude of 10 mV. Two Pt blocking electrodes were made by coating Pt paste (Heraeus, South Bend, Ind.) on the two faces of each oxide-ion conductor sample and baking at 800° C. for 1 h. All measurements were made on cooling from 900° C. down to room temperature.

Figure 3:
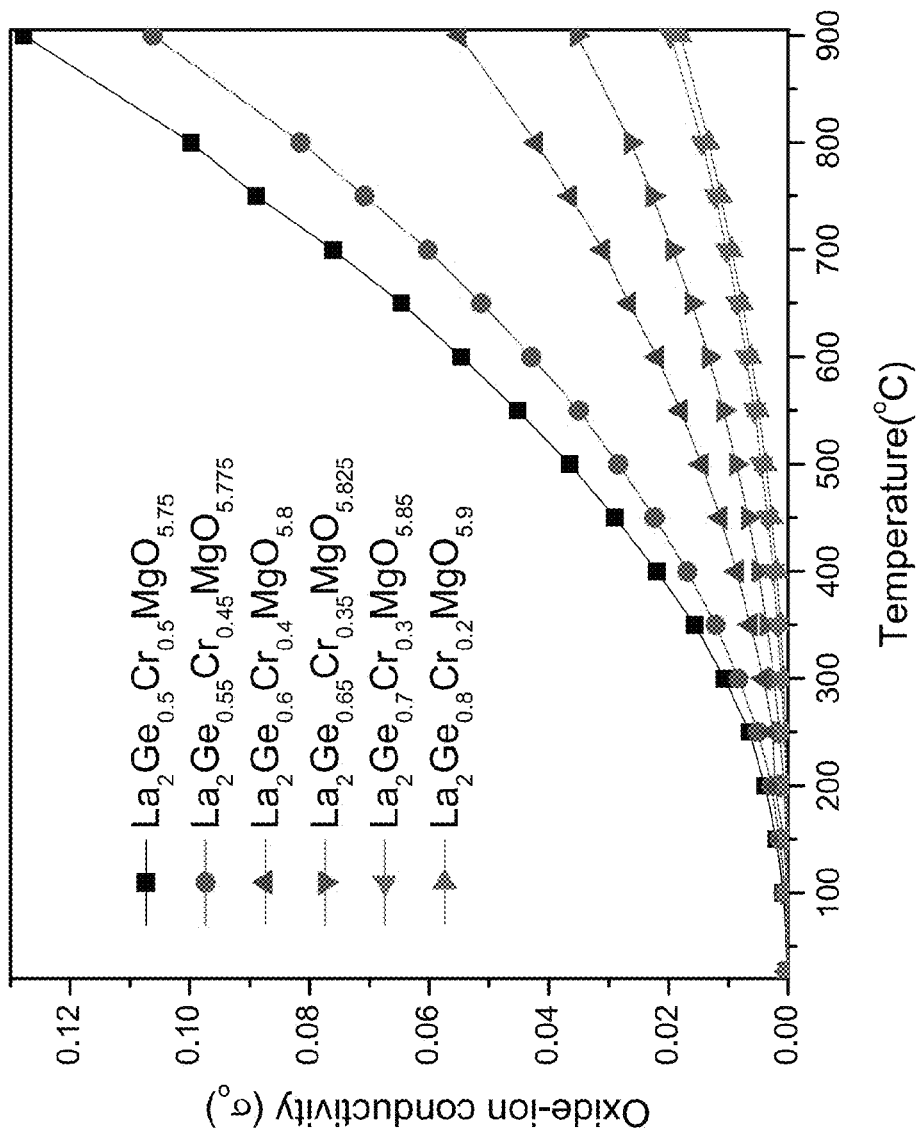
FIG. 3 presents a plot of oxide-ion conductivity ($\sigma_O$) in S/cm versus temperature in ° C. for oxide-ion conductors having the general formula $La_2Ge_{1-x}Cr_xMgO_{6-0.5x}$ in which x is between 0.2 and 0.5.

Oxide-ion conductivity measurements for oxide-ion conductors having the general formula $La_2Ge_{1-x}Cr_xMgO_{6-0.5x}$, in which $0.2\leq x\leq 0.5$ are provided in FIG. 3 and Table 2 for different temperatures. In general, increased amounts of Cr resulted in increased oxide-ion conductivity at all measured temperatures.

TABLE 2

Oxide-ion conductivity ($\sigma_O$) for $La_2Ge_{1-x}Cr_xMgO_{6-0.5x}$, in which $0 < x \leq 0.5$

| Compound | Conductivity (S/cm) | | | | | | Ea |
| --- | --- | --- | --- | --- | --- | --- | --- |
| | 300° C. | 400° C. | 500° C. | 600° C. | 700° C. | 800° c. | (eV)* |
| $La_2Ge_{0.8}Cr_{0.2}MgO_{5.9}$ | $8.29 \times 10^{-4}$ | $1.94 \times 10^{-3}$ | $3.75 \times 10^{-3}$ | $6.18 \times 10^{-3}$ | $9.43 \times 10^{-3}$ | $1.33 \times 10^{-2}$ | 0.29 |
| $La_2Ge_{0.7}Cr_{0.3}MgO_{5.85}$ | $1.19 \times 10^{-3}$ | $2.53 \times 10^{-3}$ | $4.5 \times 10^{-3}$ | $7.05 \times 10^{-3}$ | $1.03 \times 10^{-2}$ | $1.44 \times 10^{-2}$ | 0.26 |
| $La_2Ge_{0.65}Cr_{0.35}MgO_{5.825}$ | $2.33 \times 10^{-3}$ | $4.94 \times 10^{-3}$ | $8.67 \times 10^{-3}$ | $1.33 \times 10^{-2}$ | $1.94 \times 10^{-2}$ | $2.63 \times 10^{-2}$ | 0.25 |
| $La_2Ge_{0.6}Cr_{0.4}MgO_{5.8}$ | $4.11 \times 10^{-3}$ | $8.62 \times 10^{-3}$ | $1.45 \times 10^{-2}$ | $2.2 \times 10^{-2}$ | $3.09 \times 10^{-2}$ | $4.22 \times 10^{-2}$ | 0.25 |
| $La_2Ge_{0.55}Cr_{0.45}MgO_{5.775}$ | $8.34 \times 10^{-3}$ | $1.68 \times 10^{-2}$ | $2.85 \times 10^{-2}$ | $4.29 \times 10^{-2}$ | $6.02 \times 10^{-2}$ | $8.15 \times 10^{-2}$ | 0.24 |
| $La_2Ge_{0.5}Cr_{0.5}MgO_{5.75}$ | $1.07 \times 10^{-2}$ | $2.2 \times 10^{-2}$ | $3.65 \times 10^{-2}$ | $5.47 \times 10^{-2}$ | $7.61 \times 10^{-2}$ | $9.98 \times 10^{-2}$ | 0.24 |

*Ea is activations energy in electron volts (eV). Results are +/−0.01.

Figure 4:
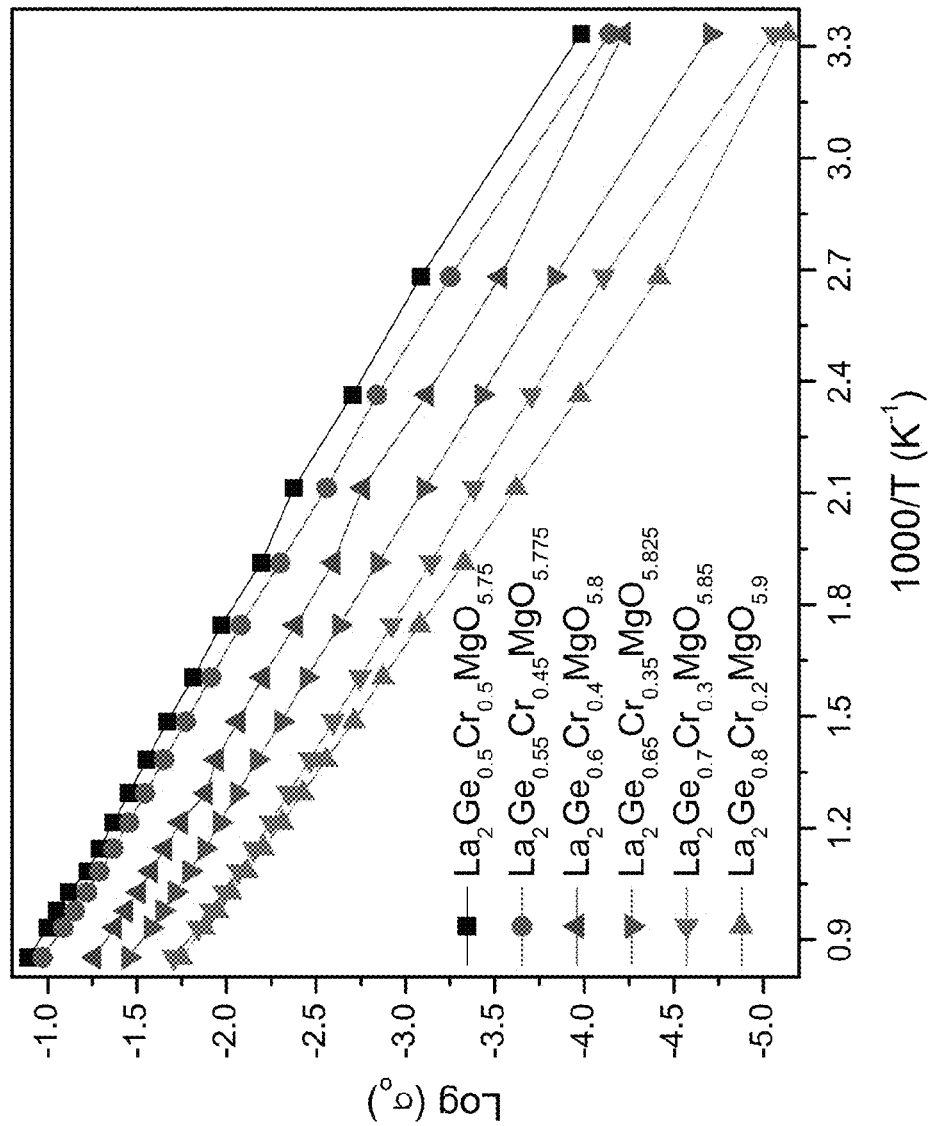
FIG. 4 presents an Arrhenius plot for oxide-ion conductors having the general formula $La_2Ge_{1-x}Cr_xMgO_{6-0.5x}$ in which x is between 0.2 and 0.5.

An Arrhenius plot (log $\sigma_O$ vs. 1000/T) for oxide-ion conductors having the general formula $La_2Ge_{1-x}Cr_xMgO_{6-0.5x}$, in which $0.2 \leq x \leq 0.5$ is provided in FIG. 4. It shows an activation energy of ca. 0.25 eV for oxide-ion transport above 300° C.

Although only exemplary embodiments of the invention are specifically described above, it will be appreciated that modifications and variations of these examples are possible without departing from the spirit and intended scope of the invention. For example, throughout the specification particular measurements are given. It would be understood by one of ordinary skill in the art that in many instances, particularly outside of the examples, other values similar to but not exactly the same as the given measurements may be equivalent and may also be encompassed by the present invention. One of ordinary skill in the art will also appreciate that the oxide-ion conductors described herein and devices containing them may operate at temperatures indicated by the data presented herein, even where such oxide-ion conductors are not chemically identical to those used to generate the data.

The invention claimed is:

1. An oxide-ion conductor having the general formula $La_2Ge_{1-x}M_xMgO_{6-0.5x}$, wherein $0<x<1$ and M is Cr, Sc, Ga, In, or a mixture thereof.

2. The oxide-ion conductor of claim 1, wherein $0<x \leq 0.5$.

3. The oxide-ion conductor of claim 1, wherein the conductor has an oxide-ion conductivity ($\sigma_O$) up to $10^{-2}$ S/cm at 300° C.

4. The oxide-ion conductor of claim 1, wherein the conductor has an oxide-ion conductivity ($\sigma_O$) up to $10^{-4}$ S/cm at room temperature.

5. A fuel cell comprising a solid electrolyte comprising an oxide-ion conductor having the general formula $La_2Ge_{1-x}M_xMgO_{6-0.5x}$, wherein $0<x \leq 0.5$ and M is Cr, Sc, Ga, In, or a mixture thereof.

6. The fuel cell of claim 5, wherein $0<x<0.5$.

7. The fuel cell of claim 5, wherein the solid electrolyte is in the form of a sheet or membrane.

8. The fuel cell of claim 5, comprising an anode containing a catalytic material operable to catalyze the formation of chemisorbed hydrogen ions from hydrogen gas ($H_2$) or chemisorbed hydrocarbon ions from a hydrocarbon.

9. The fuel cell of claim 5, further comprising a cathode containing a catalytic material operable to form oxide-ions ($O^{2-}$) from oxygen gas ($O_2$).

10. An oxygen sensor comprising an oxide-ion conductor having the general formula $La_2Ge_{1-x}M_xMgO_{6-0.5x}$, wherein $0<x<1$ and M is Cr, Sc, Ga, In, or a mixture thereof.

11. The oxygen sensor of claim 10, wherein $0<x \leq 0.5$.

12. The oxygen sensor of claim 10, wherein the oxygen sensor is operable at room temperature or above.

13. A battery comprising:
a fuel cell comprising an oxide-ion conductor having the general formula $La_2Ge_{1-x}M_xMgO_{6-0.5x}$, wherein $0<x<1$ and M is Cr, Sc, Ga, In, or a mixture thereof; and
a metal/oxide bed,
wherein the battery oxidizes the metal/oxide bed and produces electricity when discharged when the fuel cell operates in a fuel cell mode, and
wherein the battery reduces the metal/oxide bed to a metal using hydrogen gas produced when the fuel cell operates in a regenerative mode.

14. The battery of claim 13, wherein $0<x \leq 0.5$.

15. A reversible oxide-ion battery comprising:
a reductant anode;
a catalyzing current collector cathode; and
an electrolyte membrane comprising an oxide-ion conductor having the general formula $La_2Ge_{1-x}M_xMgO_{6-0.5x}$, wherein $0<x<1$ and M is Cr, Sc, Ga, In, or a mixture thereof,
wherein the electrolyte membrane separates the cathode and the anode.

16. The reversible oxide-ion battery of claim 15, wherein $0<x \leq 0.5$.

17. The reversible oxide-ion battery of claim 15, wherein the anode comprises a metal and carbon (C) composite anode.

18. The reversible oxide-ion battery of claim 15, wherein the metal comprises lithium (Li) or sodium (Na).

* * * * *